(12) United States Patent
Yanik et al.

(10) Patent No.: US 8,961,877 B2
(45) Date of Patent: Feb. 24, 2015

(54) HIGH-THROUGHPUT, WHOLE-ANIMAL SCREENING SYSTEM

(75) Inventors: Mehmet F. Yanik, Watertown, MA (US); Christopher Rohde, Cambridge, MA (US); Matthew M. Angel, Cambridge, MA (US); Cody L. Gilleland, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 940 days.

(21) Appl. No.: 12/670,882

(22) PCT Filed: Aug. 11, 2008

(86) PCT No.: PCT/US2008/072768
§ 371 (c)(1),
(2), (4) Date: Jun. 30, 2010

(87) PCT Pub. No.: WO2009/021232
PCT Pub. Date: Feb. 12, 2009

(65) Prior Publication Data
US 2010/0263599 A1      Oct. 21, 2010

Related U.S. Application Data

(60) Provisional application No. 60/954,903, filed on Aug. 9, 2007.

(51) Int. Cl.
*B01L 3/00*      (2006.01)
*G01N 33/50*      (2006.01)
*A61K 49/00*      (2006.01)

(52) U.S. Cl.
CPC ........ *G01N 33/5082* (2013.01); *A61K 49/0008* (2013.01); *B01L 3/5025* (2013.01);

(Continued)

(58) Field of Classification Search
None
See application file for complete search history.

(56) References Cited

U.S. PATENT DOCUMENTS

| 2003/0049659 A1* | 3/2003 | Lapidus et al. ............ 435/6 |
| 2003/0124505 A1* | 7/2003 | Jain et al. ............ 435/4 |

(Continued)

OTHER PUBLICATIONS

Kamath, R.S. et al., Systematic function analysis of the *C. elegans* genome using RNAi, Nature, (2003) vol. 421, pp. 231-237.

(Continued)

*Primary Examiner* — Melanie Y Brown
*Assistant Examiner* — Rebecca Martinez
(74) *Attorney, Agent, or Firm* — Sam Pasternack; MIT Technology Licensing Office

(57) ABSTRACT

Distinctive components that enable high-throughput, whole-animal screening are described. These components can be used individually or in various combinations. A staging chip strains off the excess fluid that the input animals are immersed in, increasing their density (number of animals in a given volume) and rapidly bringing them close to other fluidic components. A microfluidic sorter is adapted to isolate and immobilize a single, physiologically active animal in a selected geometry. A multiplexed micro-chamber chip receives single animals and the microchamber chip includes individually addressable screening chambers for imaging, incubation and exposure of individual animals to selected chemical compounds. An imaging structure generates sub-cellular, high-resolution images of the physiologically active animals. A well-plate interface chip is used to deliver elements from a compound library to a single output of the chip.

42 Claims, 8 Drawing Sheets

(52) U.S. Cl.
CPC ..... *B01L3/502715* (2013.01); *B01L 3/502761* (2013.01); *B01L 2200/0652* (2013.01); *B01L 2200/0668* (2013.01); *B01L 2400/0406* (2013.01); *B01L 2400/0439* (2013.01); *B01L 2400/0487* (2013.01); *B01L 2400/0655* (2013.01)
USPC .......................................................... 422/68.1

(56) References Cited

U.S. PATENT DOCUMENTS

| | | | | |
|---|---|---|---|---|
| 2004/0086427 | A1* | 5/2004 | Childers et al. | 422/100 |
| 2004/0106189 | A1* | 6/2004 | Dodgson et al. | 435/285.2 |
| 2006/0088451 | A1* | 4/2006 | Nakajima et al. | 422/131 |
| 2006/0160243 | A1* | 7/2006 | Tang et al. | 436/177 |

OTHER PUBLICATIONS

Simmer, F. et al., Genome-Wde RNAi of *C. elegans* Using the Hypersensitive rrf-3 Strain Reveals Novel Gene Functions, PLoS Biol (2003) vol. 1, pp. 77-84.

Sieburth, D. et al., Systematic analysis of genes required for synapse structure and function, Nature. (2005) vol. 436, pp. 510-517.

Kaletta, T. et al., Findng function in novel targets: *C. elegans* as a model organism, Nat Rev Drug Discov, (2006) vol. 5, pp. 387-398.

Segalat, L., Invertebrate Animal Models of Diseases as Screening Tools in Drug Discovery, ACS Chem. Biol., (2007) vol. 2, pp. 231-236.

Gray, J. M. et al. Oxygen sensation and social feeding mediated by a *C. elegans* guanylate cyclase homologue, Nature, (2004) vol. 430, pp. 317-322.

Lange, D. et al., A Microfluidic Shadow Imaging System for the Study of the Nematode *Caenorhabditis elegans* in Space, Sensors and Actuators B, (2005) vol. 107, pp. 904-914.

Heng, X. et al., Optofluidic microscopy—a method for implementing a high resolution optical microscope on a chip, Lab-on-a-Chip, (2006) vol. 6, pp. 1274-1276.

Qin. J. et al., Maze Exploration and Learning in *C. elegans*, Lab Chip, (2007) vol. 7, pp. 186-192.

Duffy, D. C. et al., Rapid Prototyping of Microfluidic Systems in Poly(dimethylsiloxane), Analytical Chemistry, (1998) vol. 70 pp. 4974-4984.

Unger, M. A. et al., Monolithic Microfabricated Valves and Pumps by Multilayer Soft Lithography, Science, (2000) vol. 288, pp. 113-116.

Dupuy, D. et al., Genome-scale analysis of in vivo spatiotemporal promoter activity in *Caenorhabditis elegans*, Nature Biotechnology, (2007) vol. 25, pp. 663-668.

Melin, J. et al., Microfluidic Large-scale Integration: The Evolution of Design Rules for Biological Automation, Annu. Rev. Biophys. Biomol Struct., (2007) vol. 36, pp. 213-231.

Yanik, M. F. et al., Neurosurgery: functional regeneration after laser axotomy, Nature, (2004) vol. 432, p. 822.

Yanik, M. F. et al., Nerve Regeneration in *Caenorhabditis elegans* After Femtosecond Laser Axtomoy, IEEE Journal of Quantum Electronics, (2006) vol. 12, pp. 1283-1291.

Rohde, C. et al., Microfluidic system for on-chip high-throughput whole-animal sorting and screening at subcellular resolution, PNAS, (2007) vol. 104, pp. 13891-13895.

Zeng, Fei et al., Sub-cellular precision on-chip small-animal immobilization, multi-photon imaging and femtosecond-laser manipulation, Lab Chip, (2008) vol. 8, pp. 653-656.

Kaletta, T. et al., *Caenorhabditis elegans* Functional Genomics in Drug Discovery: Expanding Paradigms, Model Organisms in Drug Discovery, (2003) pp. 41-73. John Wiley & Sons Ltd., West Sussex, UK.

Zhang, J. H. et al., A Simple Statistical Parameter for use in Evaluation and Validation of High Throughput Screening Assays, J. Biomol. Screen. (2007) vol. 4 pp. 67-73.

\* cited by examiner

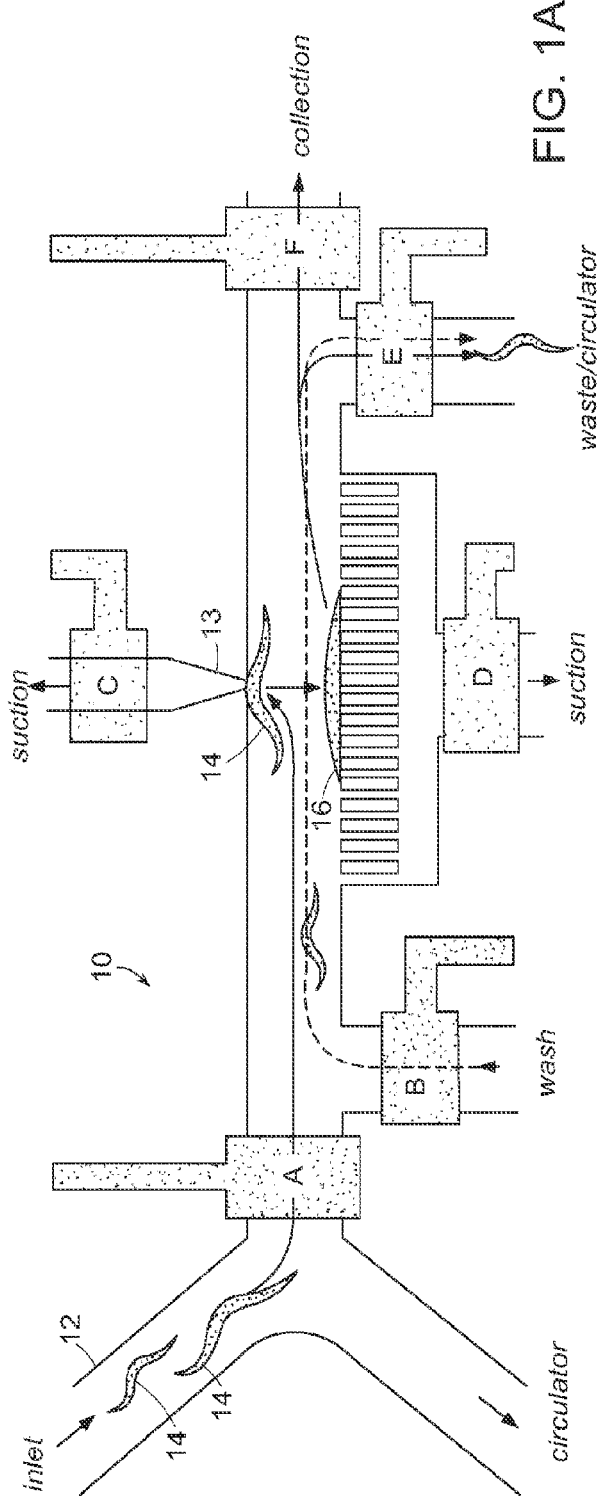
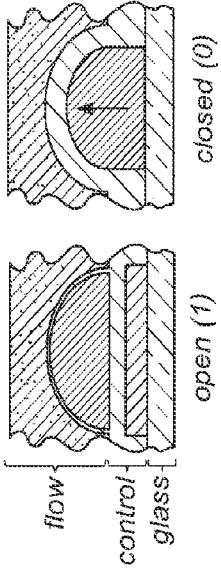
FIG. 1A
FIG. 1B

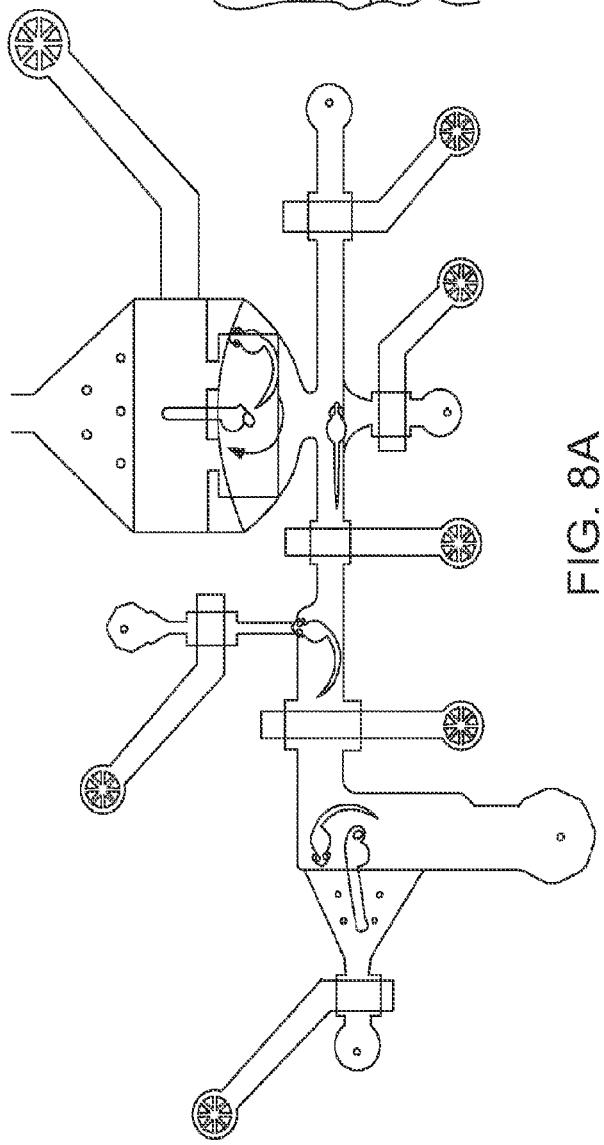
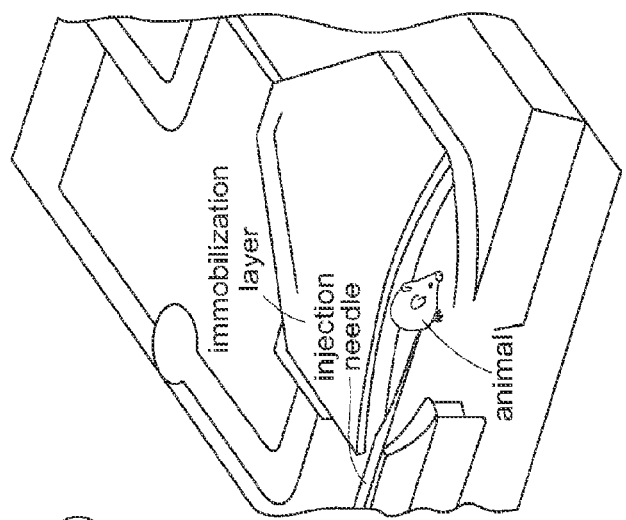
FIG. 8A
FIG. 8B

HIGH-THROUGHPUT, WHOLE-ANIMAL SCREENING SYSTEM

PRIORITY CLAIM

This application claims priority to U.S. Provisional Patent Application Ser. No. 60/954,903, filed Aug. 9, 2007, the contents of which are incorporated herein by reference.

This invention was made with government support under Grant No. DGE0645960, awarded by the NSF and under Grant No. T32 HG004947, awarded by the NIH. The government has certain rights in this invention.

BACKGROUND OF THE INVENTION

This invention relates to high-throughput screening using small-animal models. This technology can be applied to study neurotoxicity, neural degeneration, regeneration, neurological disorders, Alzheimer's disease, Parkinson's disease, wound healing, the immune system, metabolism, aging, development, stem cells, reproduction, heart diseases, vascular, liver, kidney, bladder, intestinal or tooth development. Potential applications include drug screening and discovery, population enrichment, genetic screening, and target and lead validation.

Existing large vertebrate animal models currently cannot be used in high-throughput assays for rapid identification of new genes and drug targets because of the size and complexity of the instrumentation with which these models are studied. In recent years, the advantages of using small invertebrate animals as model systems for human disease have become increasingly apparent, and have resulted in two Nobel Prizes in Physiology or Medicine during the last six years for studies conducted on the nematode *C. elegans*. The availability of a wide array of species-specific genetic techniques, along with the worm's transparency, and its ability to grow in minute volumes make *C. elegans* an extremely powerful model organism. The use of small vertebrate animals is exemplified in studies of zebrafish (*D. rerio*). Like *C. elegans*, zebrafish are transparent, develop quickly, and a wide range of genetic controls are available. Additionally, being vertebrates, zebrafish are more closely related genetically to humans, thus increasing the likelihood that any discovered process is conserved between the two.

However, the techniques to manipulate both *C. elegans* and zebrafish have not evolved with their respective fields. These manipulations are primarily manual, and performed on individual worms or fish. As a result, large-scale assays such as mutagenesis and reverse genetic screens (1-3) can take months or even years to complete manually. For example, high-throughput *C. elegans* assays are currently performed by adapting techniques developed for screening cell lines, such as flow-through sorters and microplate readers (4-6). Due to the significant limitations of these methods, high-throughput small-animal studies either have to be dramatically simplified before they can be automated or cannot be conducted at all. The numbers in parentheses refer to the references appended hereto. The contents of all of these references are incorporated herein by reference.

Existing small-animal sorters such as the BIOSORT and XL from COPAS use a flow-through technique similar to the fluorescence-activated cell sorter (FACS) technology. These systems can capture and analyze only one-dimensional intensity profiles of the animals being sorted and as a result, three-dimensional cellular and sub-cellular features cannot be resolved (13).

Although microfluidics have previously been used to perform novel assays on *C. elegans*, so far research has been limited to specific applications such as generation of oxygen gradients (7), worm culturing/monitoring during space flight (8), optofluidic imaging (9) and maze exploration (10). See also, U.S. Pat. No. 6,400,453.

Heretofore, accurate control of the nematode's or fish's microenvironment has not been possible. Such microenvironment control is necessary for making quantitative, artifact free, and repeatable measurements. Conventional techniques involve many manual steps wherein worms are exposed to different temperatures, abrupt and inaccurately timed changes. Manual handling is also error prone. All of these factors not only slow down assays dramatically, but also cause artifact errors.

It is therefore an object of the present invention to provide a high-throughput screening system for use with small-animal models.

SUMMARY OF THE INVENTION

In one aspect, the invention is a high-throughput, whole-animal screening system including a microfluidic sorter adapted to isolate and immobilize a single, physiologically active animal in a selected geometry for phenotype determination. Animals are introduced from a multi-well plate or a reservoir either directly into the sorter or into an on-chip staging area. Following immobilization, imaging, and/or manipulation in the sorter, a multiplexed micro-chamber chip receives the animal. The micro-chamber chip includes individually addressable screening chambers for exposure of individual animals to selected chemical compounds. An imaging structure is provided for generating sub-cellular, high-resolution images of the physiologically active animals. A well-plate interface chip is used to deliver compounds from a library to either the sorter or the micro-chamber chip. In a preferred embodiment, the sorter includes first suction means for immobilizing a single animal and fluid means for flushing additional animals from the sorter, either to a waste line, or back towards the input or staging area. A second suction means is provided for immobilizing the animal in the selected geometry for screening phenotype features. A layer above the main chamber in the sorter and the screening chambers that can be pressurized is provided to immobilize animals in the selected geometry for even greater stability. Fluidic means are provided for delivering the animal to the micro-chamber chip.

In another preferred embodiment, the multiplexed micro-chamber fluidic chip includes a plurality of micro-chambers, each micro-chamber including multiple barriers or posts arranged in a curved configuration to capture an animal for high resolution imaging. The preferred imaging structure includes a femtosecond two-photon capability.

It is preferred that the small animal be a nematode, such as *C. elegans* or be a small vertebrate, such as zebrafish.

BRIEF DESCRIPTION OF THE DRAWING

FIG. 1A is a schematic diagram illustrating an embodiment of a sorter used in the invention here showing the flow of a nematode through the device.

FIG. 1B is a cross-sectional view of a valve used in an embodiment of the invention.

FIGS. 8(a) and 8(b) are schematic illustrations of an embodiment of the invention particularly suited to immobilize zebrafish.

DESCRIPTION OF THE PREFERRED EMBODIMENT

The present invention utilizes small animals for high-throughput screening of biologically active materials. A preferred small animal is a nematode such as *C. elegans* or the embryos or larva of a zebrafish. Other animals that may be used in embodiments of the invention include, *Saccharomyces cerevisiae* (yeast), *drosophilla* (eggs), and other nematodes. The present disclosure will focus on *C. elegans*, but it should be noted that wherever *C. elegans* is mentioned, other small animals may be used. *C. elegans* is a preferred animal for several reasons. This animal, approximately 50 μm in diameter, can be micro-manipulated inside microfluidic chips and can be directly exposed to harsh ambient environments. This animal can survive a wide range of environmental stress, temperature ranges, pH conditions, and salinity. These animals can be kept alive for months without feeding.

The *C. elegans* worm is optically transparent so that the fate of every single cell type in the worm can be tracked through bright-field and fluorescent microscopy in vivo. The animals can be easily genetically engineered for fluorescent labeling of specific types of neurons. These animals possess all of the major neuronal cell types found in higher organisms including acetylcholine, glutamate, GABA, serotonin, and dopamine neurons. Models of Alzheimer's and Parkinson's diseases exist in the *C. elegans* system. Unknown cell-specific toxins can be classified by identifying the type of cells that they affect by both behavioral and morphological assays.

*C. elegans* has a simple enough neuronal network that there is a one-to-one map between behavioral response of the worm and the viability of specific cells. Genetic and behavioral compensatory mechanisms due to redundant pathways that exist in higher organisms are not present in *C. elegans*. Thus, the phenotypic effects are very easy to detect.

The *C. elegans* organism is self-fertilizing (Hermaphrodite) such that every worm has an identical genetic sequence (apart from any low-probability mutations). Therefore, quantitative assays can be performed correlating measurements at different time points and environments. Simple genetic manipulation techniques allow individual genes controlling specific pathways to be turned on and off selectively. This manipulation can allow rapid detection of specific biological pathways. *C. elegans* also develops quickly (three days) and has a long life span of up to three months.

Figure 4A:
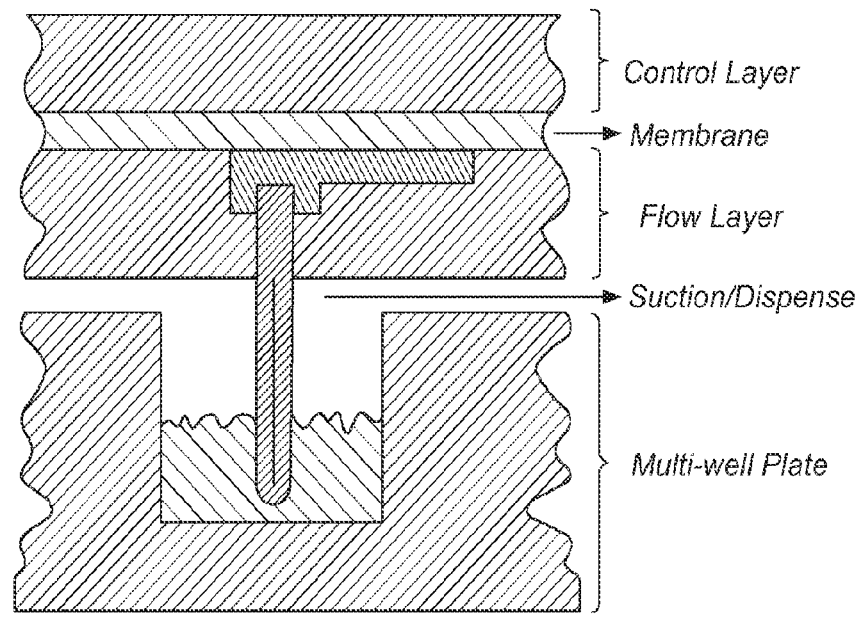
FIG. 4A is a cross-sectional view of an embodiment illustrating aspects of the multi-well-plate interface chip.
Figure 4B:
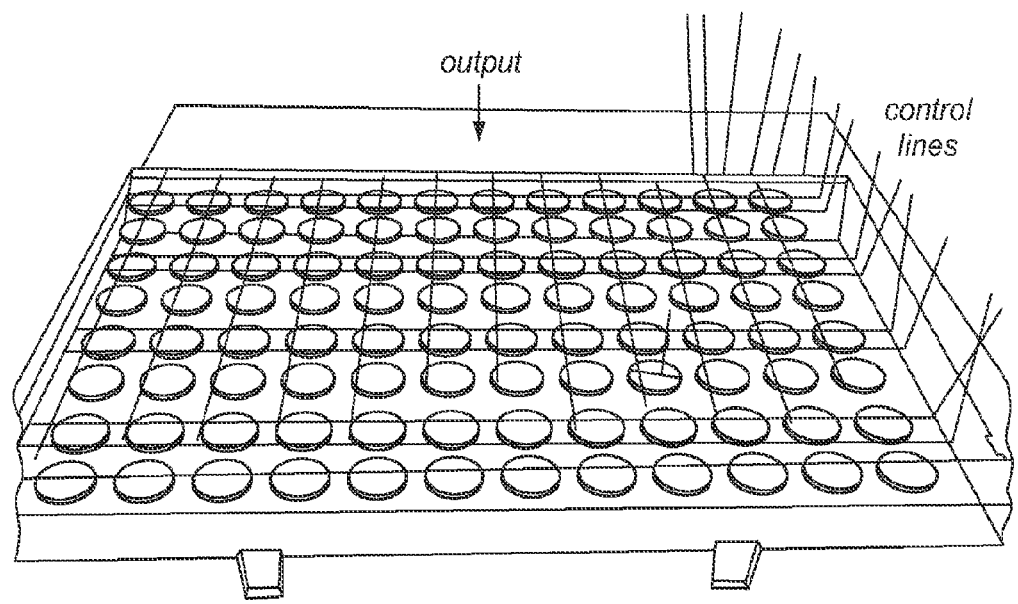
FIG. 4B is a perspective view of the multi-well-plate interface chip.
Figure 9:
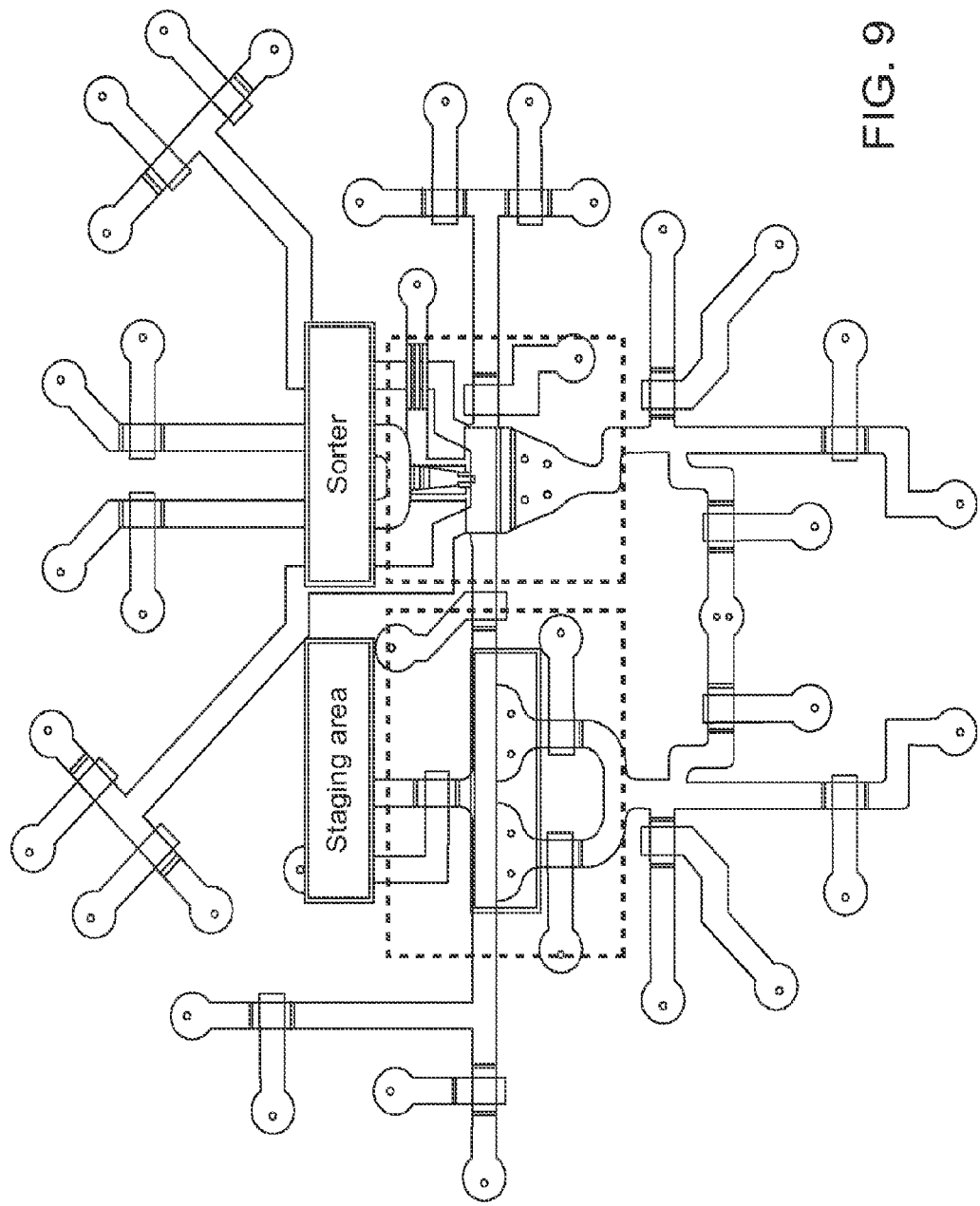
FIG. 9 is a schematic diagram illustrating an embodiment of a sorter with a staging area prior to the sorter.

With reference to FIG. 9, a staging area is composed of multiple suction channels and a plurality of microfluidic valves. Accumulating multiple animals in the staging area allows simplified tracking. With reference to the sorter designs of FIG. 1, animals still occupying the main chamber when one animal is captured by the single suction valve can be washed back to the staging area, ensuring all animals are processed and can be tracked. In the preferred embodiment, input to the staging area can be accomplished using the interface device of FIG. 4, or simply by aspirating from a reservoir or a well in a multi-well plate. The aspiration tip can be placed either manually or automatically using a computer-controlled positioning apparatus.

With reference now to FIG. 1A, a sorter 10 according to one embodiment of the invention includes an inlet 12 through which pass *C. elegans* worms 14. Fluid flow through the sorter 10 is controlled by valves labeled A, B, C, D, E and F. FIG. 1B illustrates an open and closed valve that utilizes a flexible membrane to close the valve (18).

Figures 2A, 2B, 2C:
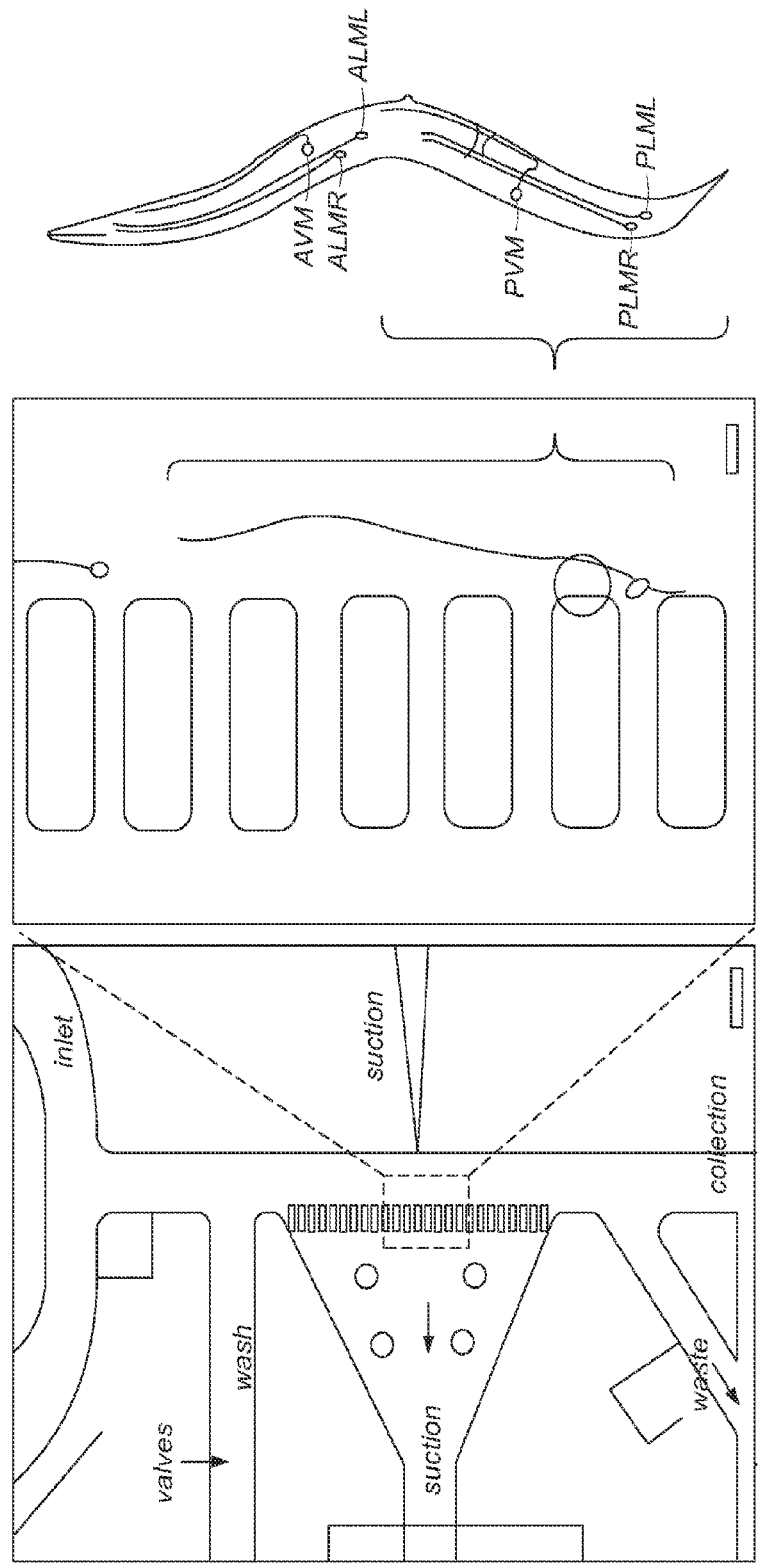
FIGS. 2A and 2B are photomicrographs of an embodiment of the sorter of the invention.
FIG. 2C is a schematic illustration of a *C. elegans* worm showing touch neurons.

Returning to FIG. 1A, when the valve A is opened worms flow into the sorter 10. Suction is applied through a microchannel 13 controlled by a valve C so that when the valve C is open a worm may be captured. The use of the single microchannel 13 eliminates the potential problem of simultaneously capturing multiple animals. Once an animal 14 is captured, valves B and E are opened establishing a flow that will sweep any other animals out of the sorter, either by continuing the flow out of the chamber, or flowing the animals back towards the input area or staging area. Upon completion of this flushing operation, valve C is closed and valve D is opened to additional suction so that the animal 14 comes to rest on a surface 16 formed by an array of suction channels. The worm 14 will be immobilized in a straight position as shown. At this point, the worm is imaged through a transparent glass or polymer substrate using high-resolution optics for phenotype analysis (see element 24 in FIG. 5A.) FIG. 2A is an image of the on-chip sorter described above in conjunction with FIG. 1A. The scale bar is 500 μm. FIG. 2B shows a single worm trapped by multiple suction channels. A combined white-light and fluorescence image is taken by a cooled CCD camera (Roper Scientific) with 6.5 μm pixels and a 100 ms exposure time through a 0.45 NA 10× objective lens (Nikon). Clearly visible are mec-4::GFP-expressing touch neurons and their processes (scale bar 10 μm). FIG. 2C shows touch neurons PLML/R and ALML/R (L, left; R, right), which extend processes along the anterior and posterior half of the worm and contribute to mechanosensation in these regions. The cell bodies are shown as black dots. Three-dimensional cross-sectioning by two-photon microscopy can also be used at the expense of sorting speed.

Figures 7A, 7B, 7C:
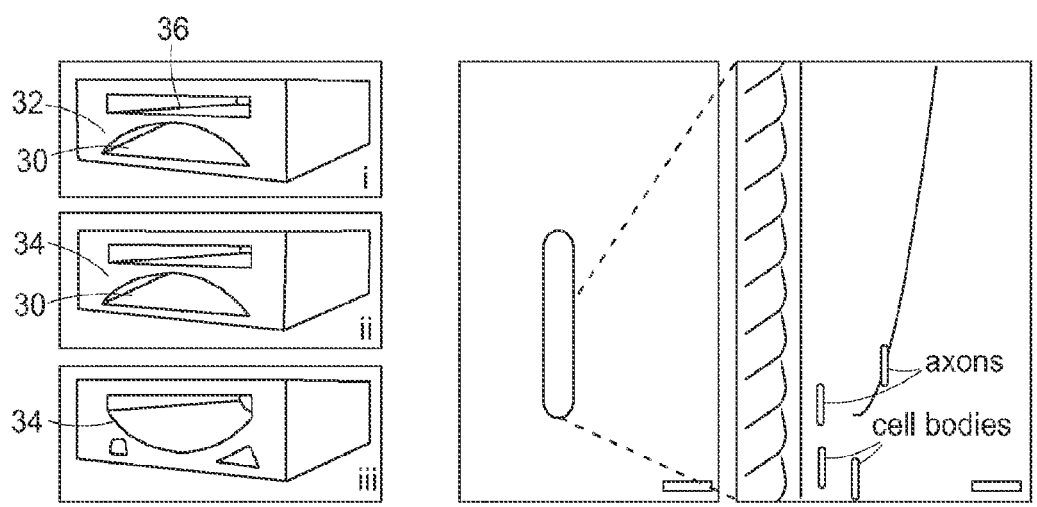
FIGS. 7(a), 7(b) and 7(c) are schematic illustrations of another embodiment of the invention utilizing a flexible membrane to fully immobilize an animal.

To achieve greater immobilization, a microfluidic valve layer can be placed above the main chamber of the sorter. FIG. 7 shows this process. Once the worm is held by the suction channels, the valve line above the sorter is pressurized. This causes expansion of the membrane separating the layers, which immobilizes the animal against the multiple suction channels. FIG. 7B and FIG. 7C show photomicrographs of an animal immobilized by an embodiment of this concept.

The microfluidic-chip sorter 10 of FIG. 1A has flow and control layers, and is permanently bonded onto a glass substrate to allow optical access, though it could also be bonded to another layer of transparent polymer. Flow layers are made by casting a room-temperature-vulcanizing dimethylsiloxane polymer (RTV615, GE Silicones) using a mold including patterned layers of negative photoresist (SU8-2025, Microchem) and positive photoresist (SIPR-7123, Shin-Etsu) on a silicon wafer. It is preferred that the main flow layer channels have a width in the range of 250-500 μm and are 80-110 μm high. The channels are rounded by reflowing the developed photoresist at 150° C. In a preferred embodiment, the flow layer includes suction channels defined using a layer of negative photoresist and that the channels are 25 μm high and 15 μm wide to allow capturing of animals. Control layers are made by casting from a mold including a patterned layer of negative photoresist (SU8-2050, Microchem) on a silicon wafer. Control channels are 70-80 μm high and the membrane that separates the two layers is 10-20 μm thick. PDMS chips cost significantly less than current flow-through animal-screening machines and can be easily incorporated into a variety of microscopy systems.

The speed of the sorter 10 depends on the actuation speed of the valves, the concentration of animals at the input, the flow speed of the worms, and the image acquisition and processing times. The technique of immobilizing worms by lowering pressure in a micro-channel is fast because the actuation speed of the valves is less than 30 milliseconds. Because of continuous re-circulation at the input, animals can be flowed at high concentration without clogging the chip. The speed of image acquisition and recognition of sub-cellular features is fundamentally limited by the fluorescence signal-to-noise ratio and the complexity of the features being recognized. The entire worm can be imaged in a single frame using a low magnification, high-NA objective lens. Cellular and sub-cellular features (touch-neuron axons, etc.) can be detected by wide-field epi-fluorescence wherein the exposure times are limited by the brightness of the fluorescent markers. Using a cooled CCD camera allows image acquisition at speeds exceeding one frame every one hundred milliseconds when imaging neurons labeled with green fluorescent protein (GFP).

Figure 3D:
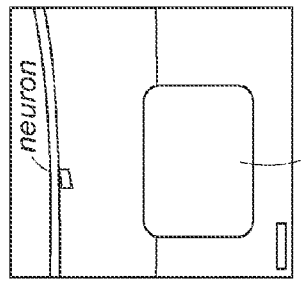
FIGS. 3A, B, C and D are photomicrographs showing an embodiment of the multiplexed micro-chamber fluidic chip of the invention.
Figure 3C:
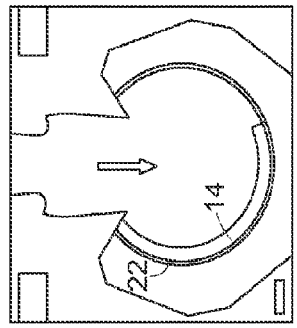
Figure 3B:
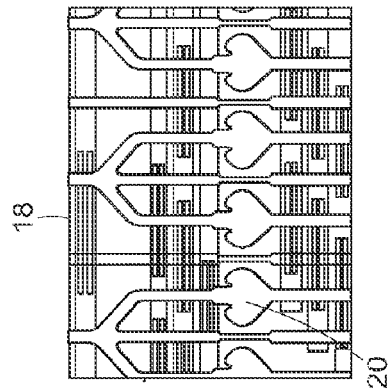
Figure 3A:
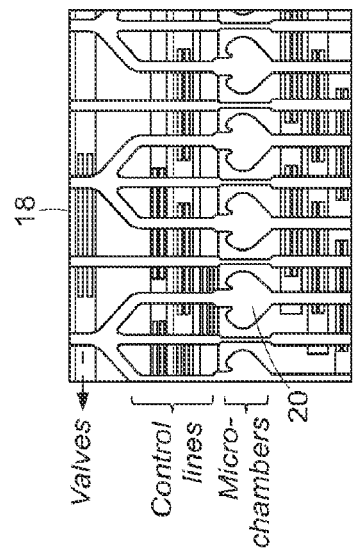

With reference now to FIGS. 3A, B, C and D a multiplexed micro-chamber chip 18 includes a plurality of micro-chambers 20. Inputs to the chambers 20 are controlled through multiplexed control lines and valves. The same inputs can be used to deliver both worms and compounds by flushing the lines with clean media. The micro-chambers 20 include barriers or posts 22 preferably arranged in a curved or circular pattern for capturing and immobilizing the worm 14 that enters the micro-chamber chip 18 upon discharge from the sorter 10. The posts 22 may be arranged in a straight configuration. The posts 22 are preferably arranged in a curved pattern to conserve space to accommodate high-throughput screening. FIG. 3C shows a close-up of a post or barrier 22 and also shows a GFP-labeled fluorescent touch neuron in an animal 14. Sorted worms from the sorter 10 are delivered to the micro-chambers 20 by opening valves via multiplexed control lines (14). Pressure in the control lines is switched on and off with external electronically controlled valves (Numatics TM series actuators). Since the number of control lines required to independently address N incubation chambers scales only with log(N) (14), micro-chamber chips based on this design can in theory be readily scaled for large-scale screening applications. Because of the millimeter scale of the micro-chambers, thousands of micro-chambers can be integrated on a single chip. As with the sorter, an additional valving layer can be placed above the individual chambers to improve the immobilization.

Each incubation chamber in this embodiment contains posts or barriers 22 arranged in an arc. To image animals, a gentle flow is used to push the animals toward the posts 22. This flow restrains the animals for sub-cellular imaging without using anesthetics. The arc arrangement of the posts reduces the size of the chambers and also positions the animals in a well-defined geometry to reduce the complexity and processing time of image-recognition algorithms. The media in the chambers can be exchanged through the microfluidic channels for complex screening strategies. Thus, precisely timed exposures to biochemicals (e.g., neurotoxins) can be performed. This capability is useful both for identifying mechanisms that rely on the action of more than one compound, and for combinatorial assays involving multiple drug targets. The use of the microfluidic technology disclosed herein also reduces the cost of whole-animal assays by reducing the required volumes of compounds used.

Interfacing microfluidics to existing large-scale RNAi and drug libraries in standard multi-well plates represents a significant challenge. It is impractical to deliver compounds to thousands of micro-chambers on a single chip through thousands of external fluidic connectors. To address this problem, the inventors herein have designed a microfluidic interface chip shown in FIG. 4A. The device includes an array of aspiration tips that can be lowered into the wells of micro-well plates shown in FIG. 4B. The chip is designed to allow minute amounts of library compounds to be collected from the wells by suction, routed through multiplexed flow lines one at a time, and delivered to the single output of the device. The output of the interface chip would then be connected to the microfluidic-chamber device 18 shown in FIG. 3 for sequential delivery of compounds to each micro-chamber 20. Combining this multi-well-plate interface chip with existing robotic multi-well-plate handlers will allow large libraries to be delivered to microfluidic chips. The same device can also be used to dispense worms into multi-well plates, simply by running it in reverse.

Figure 5A:
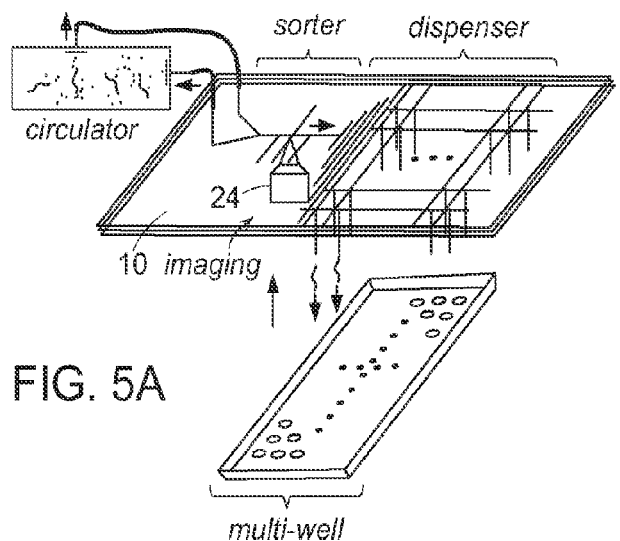
FIGS. 5A and 5B are schematic, perspective views of embodiments according to the invention.
Figure 5B:
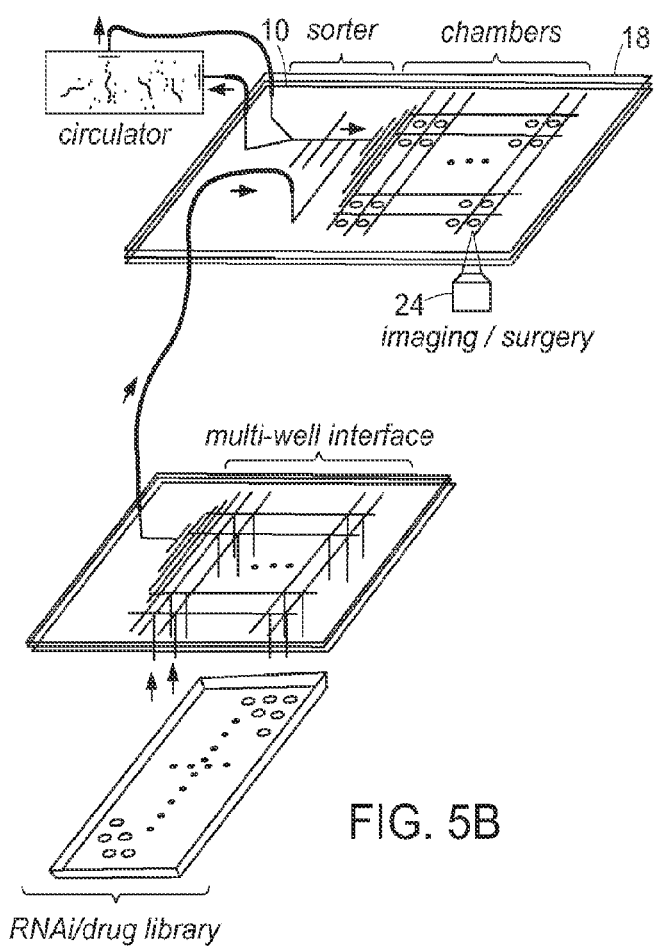

Since the sorter 10 and micro-chambers 20 disclosed herein are designed to immobilize and release animals repeatedly within few seconds, the on-chip screening technology will allow high-throughput whole-animal assays at sub-cellular resolution and with time-lapse imaging. It is possible to automate a variety of assays by combining these devices in different configurations. For example, mutagenesis screens can be performed using the microfluidic sorter 10 in combination with the microfluidic dispenser to dispense sorted animals at high speeds into the wells of multi-well plates as shown in FIG. 5A. Large scale RNAi and drug screens with time-lapse imaging 24 can be performed by combining the sorter, integrated microchambers, and multi-well plate interface chips as shown in FIG. 5B. Although *C. elegans* is self fertilizing, and has one of the lowest phenotypic variability of multi-cellular organisms (4), variations among assayed animals are still present, reducing the robustness of current large-scale screens. Sorting technology can be used to select animals with similar phenotypes (such as fluorescent-marker expression levels) prior to large-scale assays to significantly reduce initial phenotypic variations (4, 15). The micro-chamber technology disclosed herein can be used with feature-extraction algorithms to screen thousands of animals on a single chip. An interface to multi-well plates can be used to deliver large compound libraries to the micro-chambers. The system disclosed herein will allow hundreds of micro-chambers to be independently and simultaneously conditioned and monitored.

The multiple-input flow control enables both combinatorial and sequential delivery of compounds to individual chambers to allow complex screening strategies to be designed. For example, both prior to and following toxin exposure multiplexed at various stages, RNAi gene silencing can be used to turn off genes to identify biochemical pathways involved in toxicity. The microfluidic-chip system disclosed herein will be continuously kept in a stage-mounted temperature-controlled $CO_2/O_2$ incubator to allow long-term incubation of animals.

The microfluidic worm-sorter disclosed herein will also allow one to screen mutants from a large number of worm populations mutagenized and/or degenerated by toxins. One of the greatest advantages of the worm-sorter disclosed herein is that it can be interfaced with high-resolution optics easily, allowing sorting of worms accurately and with much finer phenotype analysis.

Several studies indicate that dopaminergic neurons are the neurons most vulnerable to environmental neurotoxins and are especially vulnerable to toxins that target mitochondrial proteins. In particular, it is widely accepted that sporadic Parkinson's disease results from dopaminergic-neuron death induced by environmental toxins. No organism other than *C. elegans* allows non-invasive in vivo imaging of its dopaminergic neurons. Thus, observation of dopaminergic neurons in *C. elegans* is very appealing for assessment of neurotoxicity. The inventors have performed an experiment that demonstrates on-chip detection of neurotoxicity due to the well known neurotoxin 6-OHDA. The inventors used genetically engineered worms that express GFP (green fluorescent protein) under the control of dopamine-neuron-specific promoters. Degeneration of neurons by loss of fluorescence after neurotoxin exposure is easily detectable through the transparency of the chip. In order to automatically analyze hundreds of micro-chambers, simple recognition algorithms can be used to track fates of these fluorescently labeled dopaminergic neurons.

Figure 6:
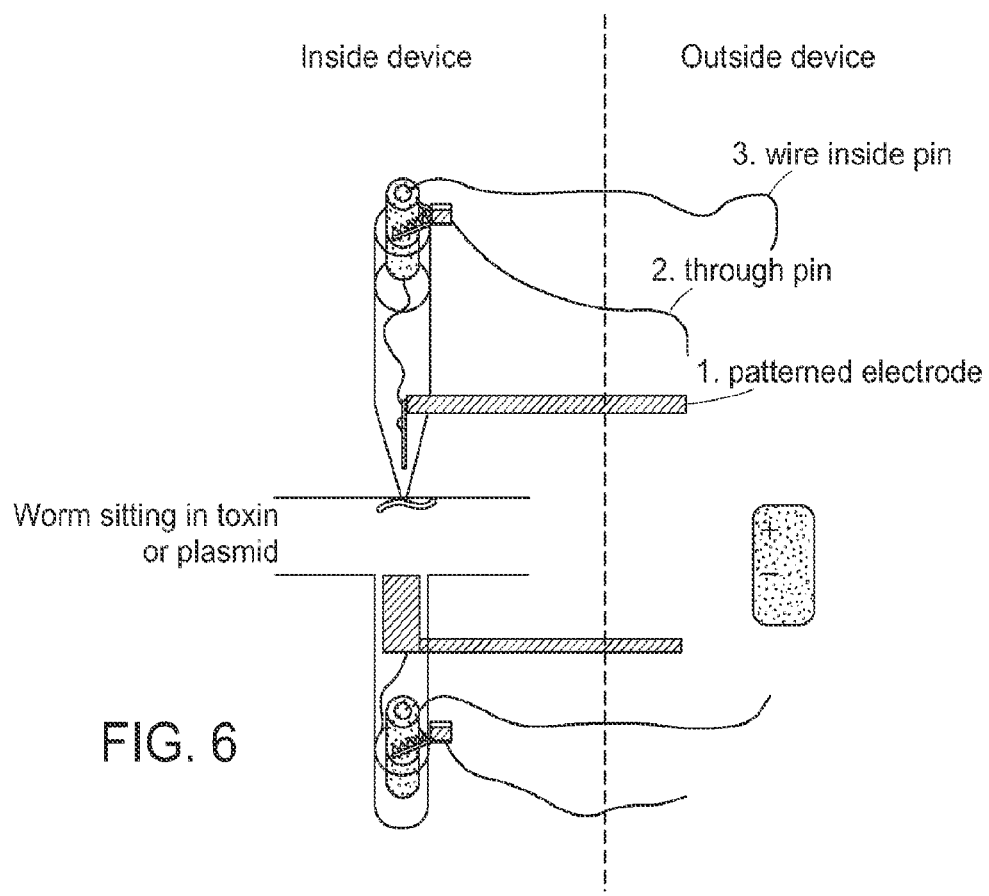
FIG. 6 is a schematic illustration of an embodiment using electroporation for toxin introduction.

FIG. 6 illustrates the use of electroporation to facilitate toxin introduction. This is done by applying an electrical potential across the worm to increase uptake of a toxin or plasmid. The electrical potential can be applied using electrodes patterned onto the substrate, via wires threaded through a pin or using the pins themselves.

The devices disclosed herein generally consist of multiple thin layers of poly(dimethyl siloxane) (PDMS) fabricated by soft lithography (19). The PDMS layers are each fabricated from a separate mold. To fabricate a flow layer suitable for smaller animals, including *C. elegans*, the inventors used a mold with two photoresist layers. First a 15 µm-thick layer of SU8-2025 negative photoresist (Microchem) was spin-coated and patterned to define the aspiration channels. Next, a 100 µm-thick layer of SIPR-7123 positive photoresist (Micro-Si) was spin-coated and patterned to create the remaining parts of the flow-layer mold. The positive part of the flow layer is rounded by reflowing the developed photoresist at 150° C. The press-down and control-layer molds were created from 65 µm- and 75 µm-thick layers of SU8-2050 (Microchem), respectively. From these molds, RTV-615 PDMS (GE Silicones) was cast. This material was deposited either by pouring (for the immobilization layer) or spinning (for the control and flow layers). Following this, the layers were cured for one hour at 80° C., then bonded together thermally for 36 hours.

Large animals, including the embryos and larva of zebrafish, can have dimensions on the order of a few millimeters. To create molds of these dimensions, channels are milled into a rigid substrate using a milling machine or laser cutter. For regions requiring rounded channels, including sections containing microfluidic valves, a ball mill with a round tip can be used. A semi-rigid plastic layer can be cast from this mold. Once cured and peeled from the rigid layer, this plastic layer can serve as a mold to create PDMS devices with channels having large dimensions. Flow, control, and immobilization layers can be created in this fashion.

With reference now to FIG. 7(*a*), a 100 µm-tall flow channel 30 contains multiple 15 µm-tall aspiration channels 32 that capture/align the animals in a linear position when the pressure in the aspiration channels 32 is lowered. This aspiration immobilizes animals only partially, and it is not sufficient to completely restrict their motion. In order to fully immobilize the animals, a seal is created around them that restricts their motion completely. This sealing is done by using a 15-25 µm-thick flexible sealing membrane 34 that separates a press down channel 36 from the flow channel 30 underneath. The press down channel 36 can be rapidly pressurized to expand the thin membrane 34 downwards, as in the microfluidic valves discussed above. The membrane 34 flexes on top of the captured animals, wrapping around them and forming a tight seal which completely restrains their motion, holding them in a linear orientation. Although the animals are constrained by the PDMS membrane 34 from the top and bottom, they still have access to liquid media by way of the multiple aspiration channels 32 on the left side. FIG. 7(*b*) shows an image of an immobilized adult animal in the device and FIG. 1(*c*) shows superimposed brightfield and fluorescent images taken at high magnification.

As discussed above, zebrafish have been recognized as a suitable model for drug screening and discovery. Zebrafish is a vertebrate animal model in which high-throughput studies can be performed due to its small size and optical transparency. Comparison of the human and zebrafish genomes suggests that a majority of human neurological disease genes and pathways also exist in zebrafish. Zebrafish models of human cardiovascular, endocrine, and brain disorders have been recently demonstrated. This animal is widely recognized as a powerful vertebrate model for dissecting the processes of neural development, neural regeneration, neural transmission and chemical toxicity. The genetic pathways involved in neural development, function and signaling pathways are highly conserved between zebrafish and humans. The use of zebrafish therefore permits otherwise impossible genetic manipulation and screening techniques in a vertebrate model. FIGS. 8(*a*) and (*b*) illustrate an embodiment of the invention particularly adapted for immobilizing zebrafish in a well-defined orientation for cellular-resolution studies. FIG. 8(*a*) illustrates the microfluidic chip layout. The chip includes a bottom flow layer where animals are routed and a control layer that turns on and off the flow in the bottom flow layer utilizing membrane valves. In a first stage, animals are loaded into the chip and in stage 2, a single zebrafish is captured by a micro-aspirator 2 while the rest of animals in the channel are removed/recycled by flushing the channel. In the next stage 3, the yoke of an animal is pushed against a wide but shallow channel by aspiration while the freely moving tail of the animal aligns toward the aspiration port. The animal is immobilized as shown in FIG. 8(*b*). Thereafter, in a stage 4, the animal is released and sent to multi-well plates for incubation. As shown in FIG. 8(*b*) after the animal is aligned in stage 3 as shown in FIG. 8(*a*), flexible PDMS membranes on top of the animal are pressurized to immobilize the animal completely. The transparent animals can then be imaged and injured at cellular resolution through a glass cover slide or polymer layer bonded to the bottom of the chip. This immobilizer can also allow micro-injection into both larvae and embryos. A pulled quartz pipette can be inserted through a molded hole in the flexible membrane on the side of the immobilizer chip. The pipette can be bonded/sealed to the membrane if desired. The flexing of the membrane permits limited motion of the pipette inside the chip.

Behavioral studies in small animals, including both zebrafish and *C. elegans*, are important for insight into a wide variety of biological processes. The high-throughput fluidic devices described above can enable many advanced behavioral studies to be performed on-chip. Behavioral responses to light, exposure to chemicals, electric shock, and mechanical stimulation can all be studied with little to no modifications to the devices discussed. Another method to study some of these responses, including response to electric shock and fluidic/air pressure, is to create a small element that can be inserted into an individual well of a multi-well plate. This is especially well suited for studies involving larger animals whose dimensions are on the order of individual wells.

REFERENCES

1. Kamath, R. S., Fraser, A. G., Dong, Y., Poulin, G., Durbin., R., Gotta, M., Kanapin, A., Le Bot, N., Moreno, S., Sohrmann, M., Welchman, D. P., Zipperlen, P. & Ahringer, J. (2003) *Nature* 421, 231-7.
2. Simmer, F., Moorman, C., van der Linden, A. M., Kujik, E., van den Berghe, P. V., Kamath, R. S., Fraser, A. G., Ahringer, J., & Plasterk, R. H. (2003). *PLoS Biol* 1, E12.
3. Sieburth, D., Ch'ng, Q., Dybbs, M., Tavazoie, M., Kennedy, S. Wang, D., Dupuy, D., Rual, J. F., Hill, D. E., Vidal, M., Ruvkun, G., and Kaplan, J. M. (2005). *Nature* 436, 510-517.
4. Kaletta T., Butler L., Bogaert T. (2003) *Model Organisms in Drug Discovery* (John Wiley & Sons Ltd., West Sussex, UK).
5. Kaletta, T., & Hengartner, M. O. (2006) *Nat Rev Drug Discov* 5, 387-398.
6. Segalat, L. (2007) *ACS Chem Biol*. 2, 231-236.
7. Gray, J. M., Karow, D. S., Lu, H., Chang, A. J., Chang, J. S., Ellis, R. E. Marletta, M. A. & Bargmann, C. I. (2004) *Nature* 430, 317-322.
8. Lange, D., Storment, C., Conley, C. & Kovacs, G. (2005) *Sensor Actuator B Chem*, 107, 904-914.
9. Heng, X, Erickson, D., Baugh, L. R., Yaqoob, Z., Sternberg, P. W., Psaltis, D. & Yang, C. (2006) *Lab Chip*, 6, 1274-1276.
10. Qin, J. & Wheeler, A. R. (2007) *Lab Chip*, 7, 186-192.
11. Duffy, D. C., McDonald, J. C., Schueller, O. J. A. & Whitesides, G. (1998) *Analytical Chemistry* 70, 4974-4984.
12. Unger, M. A., Chou, H-P., Thorsen, T., Scherer, A. & Quake, S. (2000) *Science* 288, 113-116.
13. Dupuy D. et al. (2007) *Nature Biotechnology* 25, 663-668.
14. Melin, J. & Quake, S. (2007) *Annu. Rev. Biophys. Biomol. Struct*. 36, 213-231.
15. Zhang, J. H., Chung, T. D. & Oldenburg, K. R. (1999) *J. Biomol Screen*. 4, 67-73.
16. Yanik, M. F., Cinar, H., Cinar, H. N., Chisholm, A., Jin, Y. & Ben-Yakar, A. (2004) *Nature* 432, 822.
17. Yanik, M. F., Cinar, H., Cinar, H. N., Chisholm, A., Jin, Y. & Ben-Yakar, A. (2006) *IEEE Journal of Quantum Electronics* 12, 1283-1291.
18. Rohde, C. et al. (2007) *PNAS*, Vol. 104, No. 35, 13891-13895.
19. Zeng, F. et al. (2008) *Lab Chip*, 8, 653-656.

It is recognized that modifications and variations of the invention disclosed herein will be apparent to those of ordinary skill in the art. It is intended that all such modifications and variations be included within the scope of the appended claims.

What is claimed is:

1. High throughput, whole-animal screening system comprising:
    microfluidic staging device to concentrate animals;
    microfluidic sorter adapted to isolate and/or immobilize a single animal using a mechanical means including suction;
    a multiplexed micro-chamber chip for receiving an animal from the sorter, the chip including individually addressable screening chambers, each screening chamber including structure for immobilizing animals against a plurality of spaced apart barriers arranged in a curved configuration as a result of flow through the barriers; and
    an interface chip for loading material from an external source into microfluidic devices.

2. The system of claim 1 wherein the external source is a multi-well plate.

3. The system of claim 1 wherein chambers of the micro-chamber chip are adapted to receive individual animals.

4. The system of claim 1 wherein the components of the system are adapted for incubating the animals.

5. The system of claim 1 wherein the components of the system are adapted for monitoring the animals.

6. The system of claim 1 wherein the screening chambers are adapted for exposure of the animals to compounds selected from the group consisting of biological compounds, siRNAi, shRNA, morpholino oligonucleotide, chemical compounds, synthetic compounds, neurotoxin, bacteria, virus, nanoparticles.

7. The system of claim 6 wherein the bacteria contains an RNAi vector.

8. The system of claim 6 wherein the virus contains an RNAi vector.

9. The system of claim 1 wherein the material comprises animals.

10. The system of claim 1 wherein the staging device comprises:
    fluidic means for introducing multiple animals; fluidic means for removing excess liquid from animals; and
    valves for controlling fluid flow to and from the staging device.

11. The system of claim 10 wherein the staging apparatus comprises a section of the device with a smaller dimension than the animals, allowing liquid to pass while preventing the animals from passing.

12. The system of claim 10 wherein the animals are introduced by a pressurized reservoir or aspiration.

13. The system of claim 10 wherein animals are introduced from a multi-well plate.

14. The system of claim 10 wherein the animals are output to another microfluidic device.

15. The system of claim 1 wherein the animals are introduced to the device via capillary action.

16. The system of claim 1 further including means for pressing on the animal.

17. The system of claim 16 wherein the means for pressing on the animal include a microfluidic valve.

18. The system of claim 16 wherein the region in which the immobilization occurs has a rounded profile.

19. The system of claim 1 adapted for microinjection.

20. The system of claim 19 wherein the injected material is selected from the group consisting of a chemical compound, a virus, cDNA, mRNA, RNA interference oligonucleotide, bacteria, fluorescent dye, morpholino oligonucleotide.

21. The system of claim 1 adapted for light surgery, photoactivation, or electroporation.

22. The system of claim 1 further including means to orient the animals using fluidic pressure.

23. The system of claim 1 wherein the micro-chamber chip includes a plurality of chambers that include means to capture an animal.

24. The system of claim 23 adapted for high-resolution imaging.

25. The system of claim 23 adapted for microinjection.

26. The system of claim 1 wherein the interface chip resides above a well plate, the interface chip including a separate aspiration tip placed within each individual well of the well plate.

27. The system of claim 26 further including a multiplexing microfluidic circuit providing a path between an individual well of the well-plate and another part of the system thereby enabling delivery of a plurality of compounds using only a single connection.

28. The system of claim 1 wherein the components of the system are made of polymer bonded to a transparent substrate.

29. The system of claim 1 wherein the system is incorporated with an imaging structure.

30. The system of claim 29 wherein the imaging structure is selected from the group consisting of white-light microscopy, interference microscopy, fluorescence microscopy, confocal microscopy, two-photon microscopy.

31. The system of claim 1 wherein the animal is genetically modified to express RNA.

32. The system of claim 1 wherein the animal is genetically modified to express a specific protein.

33. The system of claim 32 wherein the protein is fluorescent or photo-sensitive.

34. The system of claim 33 wherein the photo-sensitive protein is an ion channel.

35. The system of claim 1 wherein the animal is a nematode.

36. The system of claim 35 wherein the nematode is *C. elegans*.

37. The system of claim 1 wherein the animal is a vertebrate.

38. The system of claim 37 wherein the vertebrate is zebrafish.

39. The system of claim 1 used for mutagenesis screens, drug screens, viral screens, bacterial screens.

40. The system of claim 1 used for studying toxicity, neural degeneration, neural regeneration, traumatic brain injury, blunt trauma, neurological disorders, Alzheimer's disease, Parkinson's disease, amyotrophic lateral sclerosis, wound healing, immune system, metabolism, aging, development, stem cells, reproduction, heart, heart disease, bone, cancer, skin, vascular development, vasculature, liver, kidney, bladder, intestinal tract, tooth, muscle, behavior, behavioral response to light stimulation, behavioral response to controlled fluidic flow or fluidic pressure, behavioral response to electric shock, mechanical stimulation, chemical compounds, biological compounds.

41. Microfluidic device comprising: fluidic means for introducing animals to a sorter; and mechanical means for immobilizing an animal.

42. The system of claim 1 wherein the animal is a member of the genus *Drosophila*.

* * * * *